United States Patent
Rogers et al.

(10) Patent No.: US 7,810,501 B2
(45) Date of Patent: Oct. 12, 2010

(54) ORTHOTIC DEVICE FOR PREVENTING AND/OR CORRECTING DEFORMATIONAL POSTERIOR PLAGIOCEPHALY

(75) Inventors: Gary F Rogers, Walpole, MA (US); James R Miller, Miltan, MA (US)

(73) Assignees: Boston Brace, Avon, MA (US); Children's Hospital Boston, Boston, MA (US)

( * ) Notice: Subject to any disclaimer, the term of this patent is extended or adjusted under 35 U.S.C. 154(b) by 0 days.

(21) Appl. No.: 11/859,887

(22) Filed: Sep. 24, 2007

(65) Prior Publication Data

US 2008/0195203 A1    Aug. 14, 2008

Related U.S. Application Data

(63) Continuation of application No. PCT/US2006/010397, filed on Mar. 22, 2006.

(60) Provisional application No. 60/664,491, filed on Mar. 23, 2005.

(51) Int. Cl.
*A61G 15/00* (2006.01)
*A61F 5/37* (2006.01)
*A47C 16/00* (2006.01)

(52) U.S. Cl. .......................... 128/845; 128/872; 5/655

(58) Field of Classification Search ............. 5/655, 5/643, 946, 603, 731, 636, 640, 652; 128/872, 128/845
See application file for complete search history.

(56) References Cited

U.S. PATENT DOCUMENTS

| | | | | |
|---|---|---|---|---|
| 4,536,906 A | * | 8/1985 | Varndell et al. | 5/725 |
| 4,631,766 A | * | 12/1986 | Semmler et al. | 5/655 |
| 5,048,136 A | | 9/1991 | Popitz | |
| 5,107,558 A | * | 4/1992 | Luck | 5/727 |
| 5,339,472 A | * | 8/1994 | Yin | 5/636 |
| 5,524,640 A | * | 6/1996 | Lisak et al. | 5/655 |
| 6,006,380 A | | 12/1999 | Sramek | |
| 6,517,501 B1 | * | 2/2003 | Slautterback | 602/5 |
| 6,536,058 B1 | * | 3/2003 | Chang | 5/636 |
| 6,939,316 B2 | * | 9/2005 | Sklar et al. | 602/17 |
| 7,051,389 B2 | * | 5/2006 | Wassilefky | 5/636 |
| 2001/0029630 A1 | * | 10/2001 | Cortese et al. | 5/636 |

* cited by examiner

*Primary Examiner*—Patricia M Bianco
*Assistant Examiner*—Ophelia Hawthorne
(74) *Attorney, Agent, or Firm*—Medlen & Carroll, LLP

(57) ABSTRACT

The present invention is a simple, adaptable orthotic device that can correct and/or prevent deformational posterior plagiocephaly, especially if used before the infant is 4 months of age. The manufactured article provides an anatomically correcting, adjustable, concave-shaped resting surface for an infant's head in a manner that effectively eliminates uneven pressure on the infant's occiput. The orthotic device has a module design which permits easy adjustments of the devices' head cavity to accommodate differences in individual infant head size and shape, thereby providing the infant's head with a custom fit. Also, as the infant continues to grow in size, the adjustable head cavity and torso recess features of the orthotic device allow the contoured spatial volume and dimensions of the molded supporting surfaces to expand as the infant's calvaria grow; and thereby facilitate a progressive, normalization and rounding of the infant's occiput.

4 Claims, 10 Drawing Sheets

ORTHOTIC DEVICE FOR PREVENTING AND/OR CORRECTING DEFORMATIONAL POSTERIOR PLAGIOCEPHALY

CROSS-REFERENCE TO RELATED APPLICATIONS

This application is a Continuation application of a co-pending International application No. PCT/2006/010397, filed Mar. 22, 2006, which designated the U.S., and which claims the benefit under 35 U.S.C. §119(e) of U.S. Provisional Application No. 60/664,491, filed Mar. 23, 2005, which are herein incorporated by reference.

FIELD OF THE INVENTION

The present invention is concerning generally with manufactured articles useful as a prophylactic against and treatment for pediatric development disorders; and is particularly directed to orthotic devices for preventing or correcting deformational posterior plagiocephaly.

BACKGROUND OF THE INVENTION

The Medical Need:

The "Back to Sleep" campaign has been a great success, reducing the number of infant deaths from Sudden Infant Death syndrome ("SIDS) by 25% since its inception in 1992. By one estimate, the risk of death due to SIDS is two times greater while sleeping in a prone position than when the child lies in a supine position. Perhaps then, it not surprising that for infants sleeping in a prone position the death rate declined from 70% in 1992 to 24% in 1996 [National Center for Health Statistics, Center for disease Control and Prevention].

Along with positional advice, the American Academy also recommends avoiding soft and gas trapping surfaces in cribs and eliminating "tummy time" while the infant is awake. Under certain circumstances (such as gastroesophageal reflux, upper respiratory tract obstructions or infectious diseases, etc), a pediatrician may weigh the risks and recommend a prone position. However, one side effect of the "Back to Sleep" campaign has been the marked rise of plagiocephaly, and deformational posterior plagiocephaly in particular [Pollack et al., "Diagnosis and Management of Posterior Plagiocephaly", *Pediatrics*, Vol. 99, No. 2, February 1997].

The Problem of Plagiocephaly:

Plagiocephaly typically progresses most in infants ranging between birth and 3-4 months of age. Deformational posterior plagiocephaly is a localized flattening of the cranium, usually near the occiput. This pathological condition is illustrated by FIGS. 1A and 1B respectively.

As seen therein, FIG. 1A provides an overhead view of an infant with deformational plagiocephaly; and FIG. 1B schematically illustrates the positional deformation of the soft infant cranium causing unilateral flattening in the parieto-occipital region, anterior advancement of the ipsilateral ear, and associated anterior displacement of the ipsilateral forehead.

Deformational posterior plagiocephaly occurs most often in infants of four months age or younger because (i) the skulls of young infants are still easily deformed; (ii) the posterior calvaria are rapidly expanding against a flat surface; and (iii) such infants are neuromuscularly immature and lack the coordination to shift their head position. If left uncorrected the pressure forces will likely remain continuously applied until the infant reaches 6-8 months of age, whereupon the existing deformation will likely become permanent.

Infants with torticollis (wry neck) are particularly at risk for posterior plagiocephaly since their condition will make them favor turning their head one way. By definition, torticollis is a congenital or acquired condition of limited neck motion in which the child will hold the head to one side with the chin pointing to the opposite side; and is the result of the shortening of the sternocleidomastoid (neck) muscle. Thus, as a consequence of the positioning of the head continually in one side position, the infant suffers from the flattening of that side of his head. This asymmetrical plagiocephaly is particularly disfiguring in appearance.

It as been recognized that the vast majority of infants with occipital flattening do not have Craniosynostosis—a premature obliteration of the sutures which results in skull deformity and potential restricted growth of the brain. Also, Lamboid Synostosis, which can mimic deformational posterior plagiocephaly, is remarkably rare, occurring only in an estimated 20 per million live births. Thus, occipital flattening is about 5000-8000 times more likely to occur from a deformation process than from a sutural fusion.

Incidence of Posterior Plagiocephaly:

The incidence rate of posterior plagiocephaly in some infant populations can be as high as 48%. By contrast, the incidence rate of craniosynostosis is only about 1 in 3,000 infants [Bruneteau, R J. & J. B. Mulliken, "Frontal Plagiocephaly: Synostotic, Compensational, Or Deformational", *Plastic and Reconstructive Surgery* 89(1):21-31 (January 1992)].

Actual incidence rates vary by patient population and age; and will be influenced by cultural habits for positioning resting newborns. Also as with all diseases the severity of the posterior plagiocephaly comes in degrees. Nevertheless any kind of plagiocephaly is very unnerving for parents to live with.

Research at Children's Hospital and Harvard Medical School in 2002 by Dr. Peitsch and others indicated that 13% of all single-birth newborns and 56% of all twins had localized cranial flattening, a possible precursor to posterior plagiocephaly [Peitsch et al., "Incidence of Cranial Asymmetry in Healthy Newborns", *Pediatrics* 110(6):e72 (December 2002)]. A further 10% of all infants suffer from congenital torticollis, which will exacerbate a tendency towards posterior plagiocephaly.

Furthermore, about 25,000 infants are referred to us specialists every year for treatment from plagiocephaly. With 4.6 million live births in the U.S. annually, there are likely to be at least 600,000 infants born each year in need of corrective treatment for plagiocephaly; and prophylactic measures to prevent or avoid deformational posterior plagiocephaly would benefit all newborns.

Conventionally Known and Used Therapeutic Techniques:

As conventional corrective measures, the overwhelming majority of infants with occipital flattening have been treated to date using therapies that redistribute the weight-bearing load on the posterior calvaria. The therapies typically include several different categories or techniques. These include the following general categories:

(A) Simple positioning and re-positioning therapy which encourages parents to shift the infant's sleep position periodically through the sleep periods;

(B) The use of wedge or doughnut shaped support pillows that redirect the pressure of the head in its resting position to the side of the head;

(C) The use of tiltable mattresses or beds that relieve the pressure on the occipital prominence of the head and distribute the pressure over a wider surface area; and (D) The use of orthoplastic helmets or headbands that apply differential pressure to the head of an infant.

Because plagiocephaly typically progresses most in infants ranging in age from birth to about 4 months, many physicians recommend infant repositioning and observation, presumably because there is hope of spontaneous correction; and because the infant may be viewed as being too underdeveloped for helmet therapy.

Also, anxious parents often purchase off-the-shelf orthotics and wedges in an attempt to prevent further deformation of their baby's head and face. However, most parents report poor results using these modalities; and eventually seek further medical consultation with a specialist. In true fact, there is no clinical data available to date which substantiates the alleged corrective benefits of any commercially sold orthotic, other than the molding helmet.

In addition, while the molding helmet is effective to treat moderate or severe cases of deformational plagiocephaly, such helmets are far too costly and cumbersome for use in minor cases, or as a prophylaxis in high-risk patients (i.e., early plagiocephaly, severe torticollis, premature infants, etc.). Additionally, insurance companies are less inclined to cover the cost of the molding helmet since, in their opinion, such calvarial flattening is considered to be merely "cosmetic".

RELEVANT PUBLICATIONS

The published literature provides many descriptive instances for these various approaches. Merely as an aid, a summary of some relevant legal publications includes the following:

Illustrating the use of shaped support pillows for Category B above are: U.S. Pat. Nos. 6,052,849; 6,473,923; 6,564,408; 6,006,381; 6,226,817; 6,460,207; and Published U.S. Patent Applications Nos. 2002/0042954 A1, and 2004/0172762 A1.

Representing the use of tiltable mattresses or beds for Category C above are: U.S. Pat. Nos. 6,421,855; 6,260,553; D448,227; 5,581,832; and Published U.S. Patent Applications Nos. 2003/0033674 A1, 2001/0042269 A1, 2002/0174488 A1, and 2003/0145384 A1.

Exemplifying the use of orthoplastic helmets and headbands for Category D above are: U.S. Pat. Nos. 4,776,324; 6,592,536; 6,266,832; 5,094,229; 5,038,312; 5,915,503; 6,346,353; and Published U.S. Patent Applications Nos. 2003/0195450 A1, and 2004/0015118 A1.

Nevertheless, despite all these developments to date, there remains a recognized and continuing need for further improvements in devices and procedures which can correct and/or prevent deformational posterior plagiocephaly. All such improvements in such singular medical devices and effective treatment techniques would be readily seen as a major contribution and outstanding benefit in this medical field.

SUMMARY OF THE INVENTION

The present invention has multiple aspects.

A first aspect of the present invention provides an orthotic device for treating posterior plagiocephaly in an infant, said orthotic device comprising:

a base substrate having fixed dimensions and configuration, and comprising at least one thermoformable material having a density sufficient to maintain its material integrity under load;

an anatomically correcting head cavity molded into said base substrate ale to receive and support the occiput of an infant's head, said anatomically correcting head cavity presenting a molded maximal contoured outline and spatial volume for normalizing and rounding the occiput of an infant's head;

a plurality of discrete layers of material serving as a series of prepared individual liners which can be positioned in overlay series on-demand within the molded spatial volume of said head cavity, can be individually removed at will from the positioned overlay series lying within the spatial volume of said head cavity, and, via their presence within said head cavity, can alter the available contoured outline and spatial volume presented by said head cavity for normalizing and rounding the occiput of an infant's head; and a bridge section of constant dimensions and configuration which is disposed on said base substrate adjacent to said head cavity and serves to support the neck of a infant during the normalizing and rounding of the occiput in an infant's head.

A second aspect of the present invention provides an orthotic device for treating posterior plagiocephaly in an infant, said orthotic device comprising:

a base substrate having fixed dimensions and configuration, and comprising at least one thermoformable material having a density sufficient to maintain its material integrity under load;

an anatomically correcting head cavity molded into said base substrate ale to receive and support the occiput of an infant's head, said anatomically correcting head cavity presenting a contoured outline and spatial volume of molded maximal dimensions for normalizing and rounding the occiput of an infant's head;

a plurality of discrete layers of material serving as a series of prepared individual liners which can be positioned in overlay series on-demand within the molded spatial volume of said head cavity, can be individually removed at will from the positioned overlay series lying within the spatial volume of said head cavity, and, via their presence within said head cavity, can alter the available contoured outline and spatial volume presented by said head cavity for normalizing and rounding the occiput of an infant's head;

an anatomically correcting torso recess molded into said base substrate ale to receive and support the torso of an infant's body, said anatomically correcting torso recess presenting a spatial volume having fixed width and length dimensions and a molded maximal depth dimension for supporting the infant's torso;

a plurality of discrete layers of material serving as a series of prepared individual liners which can be positioned in overlay series on-demand within the molded depth dimension of said torso recess, can be individually removed at will from the positioned overlay series lying within the molded depth dimension of said torso recess, and, via their presence within said torso recess can alter the available dimensional depth presented by said torso recess for supporting an infant's torso; and a bridge section of constant dimensions and configuration which is disposed on said base substrate adjacent to said head cavity and said torso recess which serves to support the neck of a infant during the normalizing and rounding of the occiput in an infant's head.

BRIEF DESCRIPTION OF THE FIGURES

The present invention can be more easily understood and better appreciated when taken in conjunction with the accompanying Drawing, in which.

DETAILED DESCRIPTION OF THE INVENTION

Figure 1B:
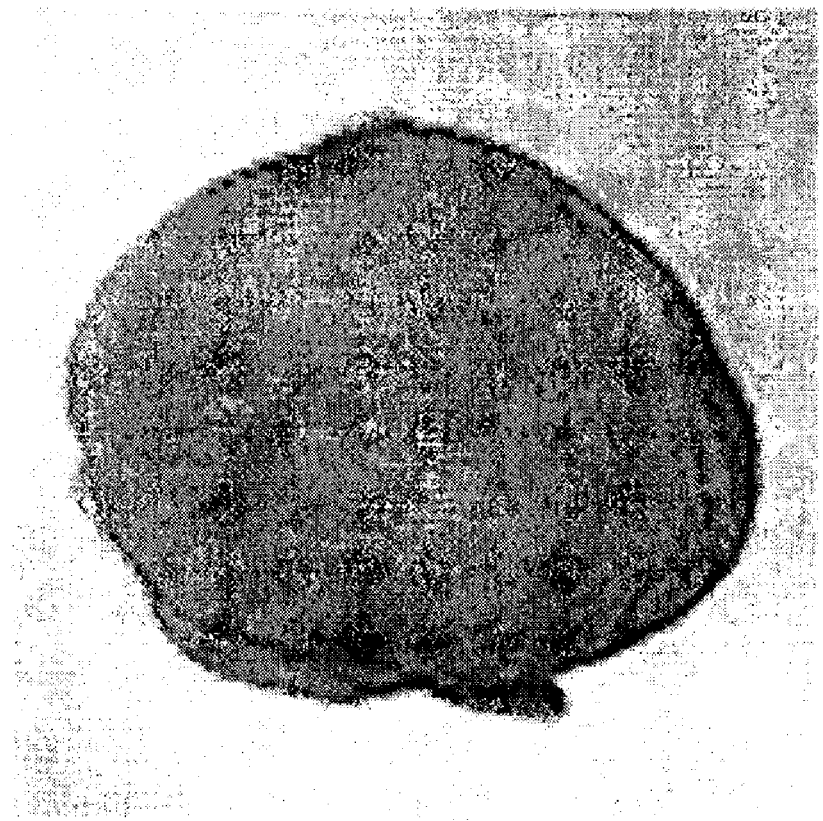
FIG. 1B is a schematic illustration demonstrating positional deformation of the soft infant cranium causing unilateral flattening in the parieto-occipital region, anterior advancement of the ipsilateral ear, and associated anterior displacement of the ipsilateral forehead.
Figure 1A:
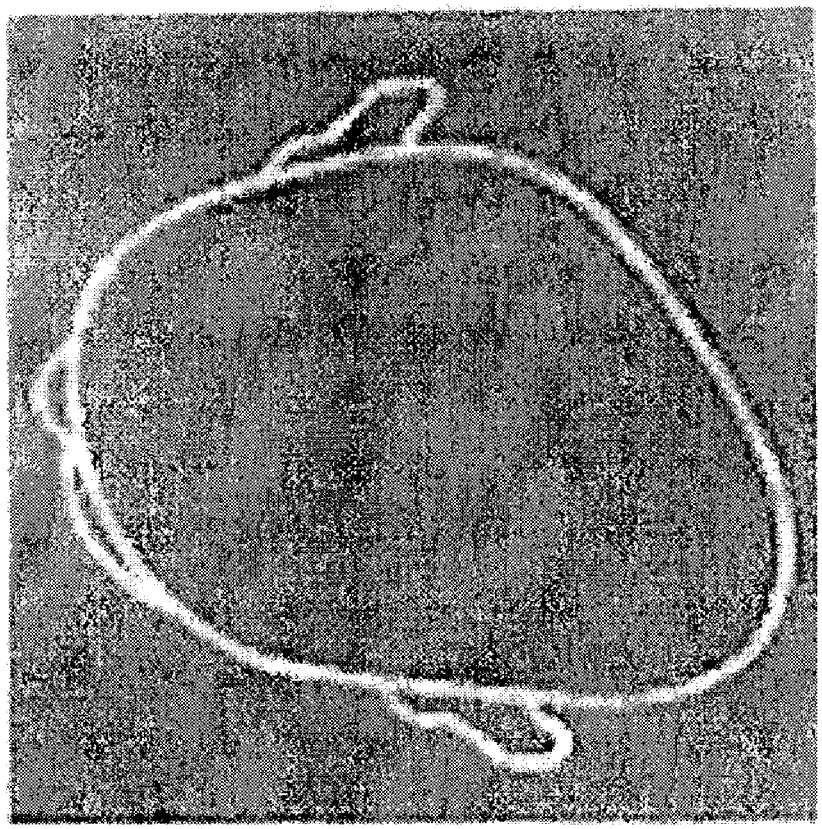
FIG. 1A is an overhead view of an infant with deformational plagiocephaly.

The present invention is a simple, adaptable orthotic device that can correct and/or prevent deformational posterior plagiocephaly, especially if used before the infant is 4 months of age. The manufactured article is an anatomically correcting, repeatedly adjustable, concave-shaped resting surface for an infant's head in a manner that effectively eliminates uneven pressure on the infant's occiput.

Equally important, the orthotic device has a modular design which permits easy initial adjustment(s) of the head cavity to accommodate differences in individual head size and head shape, thereby providing the infant with a personalized custom fit. Thus, as the infant grows and develops over time, the adjustable head cavity feature of the orthotic device allow the contoured spatial volume and dimensions of the molded supporting surfaces in the orthotic device to expand and enlarge as the infant's calvaria grow; and thereby facilitate a progressive, normalization and rounding of the infant's occiput. In addition, the posterior neck area of the infant is supported by a fixed bridge section, which also serves to off-load or reduce contact pressure between the rest surface and the occiput, especially as the cavity of the device deepens.

The present invention thus provides a number of different major advantages and unusual benefits for the user. These include:

1. None of the conventionally available plagiocephaly corrective supports allow for a size-adjustable molded support which can be changed over time. One size cannot provide an appropriate molding surface for all infants of any age; and therefore, one size fits none. In contrast to other devices, such a size-adjustable feature and capability is provided by the present orthotic device, and an adjustable surface can be fashioned via the use of removable individual layers of material.

2. The conventionally available plagiocephaly corrective supports are typically manufactured using extremely soft substances, such as soft foam or fiber-filled pillow material. Although the soft and comfortable feel of these materials is reassuring to the parents of the infant, these types of substances do not provide sufficient firmness to maintain the corrective cavity form needed to mold the infant's skull.

In comparison, the present orthotic device is firm, durable and biocompatible; and provides a pressure-resistant, molded head cavity which is an anatomically correcting template for the proper reshaping of the infant's head. This is a unique feature and function of the orthotic device.

3. It is recognized and accepted that the conventionally known wedge shaped pillows can enforce side-to-side sleep position, but cannot serve as a mold for the correct had shape. Similarly, the dough-nut shaped pillows can prevent infant head turning, but do not correctly normalize and round the head shape of the infant; instead, they merely create "dough-hole" protuberances onto the back of the infant's skull.

4. The expandable shape of the present invention allows for the use of one bed, pad, or mattress over many weeks or months time. This cost saving can be considerable.

5. The present invention is neither cumbersome nor difficult to use; and will provide an improved compliance by the parents of the infant and a grater probability for a successful treatment and correction of deformational posterior plagiocephaly.

I. The Structural Features of the Orthotic Device

The orthotic device comprising the present invention is a firm, molded support article having at least one, and preferably two, specifically configured concave hollows or molded depressions into which the infant's head—and preferably the infant's torso as well—will fit snugly, while the infant lies in a supine position (i.e., lying prone or face upwards).

A First Embodiment of the Orthotic Device

A first illustrative example of the orthotic device is shown by FIGS. 2-5 respectively. As seen therein, the orthotic device appears as prepared bed, pad, or mattress 2 comprising an underlying base substrate 10; an anatomically-correcting concave head cavity 12 which is shaped and sized to receive and support at least the parieto-occipital region of the infant's head; an anatomically-correcting concave torso recess 14 which is configured and dimensioned to receive and support the infant's neck and shoulders; and a neck bridge section 16 lying between and adjacent to each respective concave spatial depression 12, 14.

The Base Substrate

In preferred embodiments of the prepared bed, pad, or mattress, the overall base substrate 10 is a planar tier (or alternatively a stage or sheet) of fixed dimensions. This planar tier is desirably about 75 mm in thickness because the overall fixed dimensions of the base substrate 10 must provide two different capabilities: the base substrate must be sufficient in thickness (as well as having sufficient length and width) to hold and contain the largest spatial volume and deepest perimeter/contour outline which is anatomically corrective for both the head cavity 12 and the torso recess 14 respectively; and the base substrate also must be adequate in material substance to support the infant's head and torso when these body parts are placed into the anatomically-corrective molded spaces intended to receive them.

Accordingly, to achieve this purposes it is intended and expected that the planar tier comprising the base substrate 10 will be constructed of a firm biocompatible and durable composition (or an admixture of different chemical compositions) that does not permit substantial pressure distortion; is able to function as an underlying supportive stage or sheet of material; and will typically vary in overall thickness from about 50-100 mm.

The Molded Maximal Spatial Volumes for Receiving the Head and Torso

The molded head cavity 12 and the molded torso recess 14 respectively define two different, specially configured, maximal spatial volumes whose individual dimensions, depth, contours, and perimeter size are encompassed and controlled by at least one surrounding, molded solid wall. This molded, maximum-volume, solid material wall, (or, in the alternative, walls) is composed of a firm biocompatible and durable material that does not allow for meaningful pressure distortion of the shaped contours and perimeters defining these anatomically-correct concavities.

In this manner, by maintaining the purposeful concave shape and maximal volume of the head cavity 12 and of the torso recess 14, the orthotic device serves as an anatomically-correcting medical article; and provides a prepared therapeutic/prophylactic template against which the occipital bones in the infant's head can normalize and become rounded over time.

In effect, the concave spatial depressions of the orthotic device act to alter the shape of the infant's growing calvaria. The dimensions and configuration of the molded spatial depression constituting the head cavity 12 will off-load pressure from the flattened area then existing (or threatening to become present) in the infant's skull; and the shape of the infant's head will grow more symmetric and rounded over time, until the infant's head shape ultimately conforms to the anatomically-correct configuration of the concave head cavity (which is perfectly concave and formed to a cephalic index, or width/length ratio, of 0.75).

Accordingly, as the flattening of the skull corrects over time, the infant's occiput will experience even pressure from all sides of the concave cavity. Hence, by employing the same deformation mechanism that caused the initial flattening of the infant's head (calvarial growth against a flat surface), the concave cavity 12 serves as a head support and produces occipital rounding (calvarial growth against a concave surface).

Multiple Layers of Solid Material

The concave head cavity 12 and the torso recess 14—the molded maximal spatial volumes intended to receive the head and torso of the infant respectively—are modified, controlled, and formed using multiple layers 20 of individual material inserts which are arranged and aligned in overlay series. In each of these concavities, the individual material layers 20 will be positioned one over the other as multiple strata in overlay array series, and typically will appear as an arranged stack of layers 22.

Thus, it is expected that when constructing the exemplary embodiment shown by FIGS. 2-5 respectively, one or more successive layers (of solid material) are initially present and collectively will form part of the solid material wall which then encompasses, dimensions, and quantitatively defines the spatial volume then existing within each molded depression. Via this arrangement, each discrete layer 20 (of solid material) can be retained if so desired; or alternatively, each discrete layer can be individually removed on-demand to enlarge the presently existing total spatial volume and concomitantly increase the depth of either (or both) the head cavity 12 and the torso recess 14 to accommodate the head and body changes which invariably occur as the infant grows in age and size. Furthermore, any previously removed layer 20 also can be optionally re-inserted into the stacked array at will to decrease an earlier-made modification of spatial volume.

This capability either to retain if desired, or to remove at will, and optionally to re-insert if needed, one or more individual layers of material repeatedly on-demand for either or both molded spatial depressions is an unique capability and structural feature. This capability allows the parent or child caretaker to modify each spatial volume separately, such that the head cavity and the torso recess becomes individually fitted and custom sized multiple times over time to meet the ever changing size requirements of the infant's growing head and torso.

It will be appreciated therefore that, in preferred constructions of the head cavity 12 and of the torso recess 14, eight individual layers 20 of material have been placed into an array 22 and used to advantage within each molded concavity; and this array 22 of eight layers generates an alterable on-demand solid material wall which, on each occasion of alteration, differently encompasses and defines the volume and depth dimension then present for each of the molded spatial depressions.

In these preferred examples, each discrete layer of material is typically about 3-4 mm thick. However, it is expected and intended that each individual material layer in employed in series may range from 2-6 mm in thickness; that the number of individual material layers arranged in such overlay series (i.e., as a stack) may routinely vary from 3-12 discrete layers.

The Neck Bridge Section

In this embodiment, the molded spatial depressions 12, 14 intended to receive and support the head and torso of the infant are optionally, but preferably separated by a discrete bridge section 16, which is comprised of firm support material and upon which the back of the infant's neck is intended to rest. When present, this neck bridge section 16 is not adjustable in thickness (girth) or height; and will not affected if and when one or more successive layers of material originally present as part of the head cavity 12 and the torso recess 14 are removed. Accordingly, the neck bridge 16 spanning the distance between the two spatial volume depressions 12, 14 should always remain at one fixed height By this structural relationship, the depth of the head cavity 12 and the torso recess 14 relative to the bridge section 16 becomes increased as each individual layer of material is successively removed from the two spatial depressions, but the height of the bridge section itself remains constant and uniform. This constancy of neck bridge height and support—despite the ever increasing deepening of the head cavity 12 and the torso recess 14—is a singular feature which allows the infant's head and body to remain level; and also prevents the infant's head from being pushed towards its chest as the infant's head grows in size over time.

A Second Embodiment of the Orthotic Device

Figure 6:
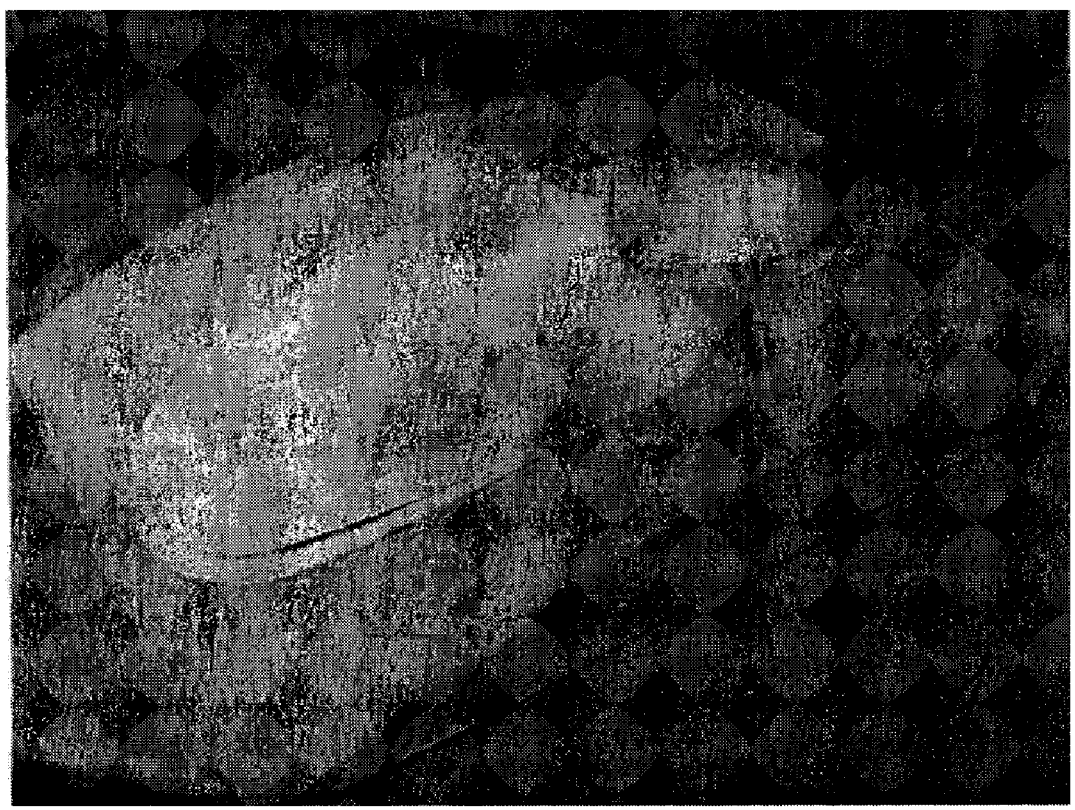
FIG. 6 is an overhead view of a second preferred embodiment of the orthotic device comprising the present invention.
Figure 7:
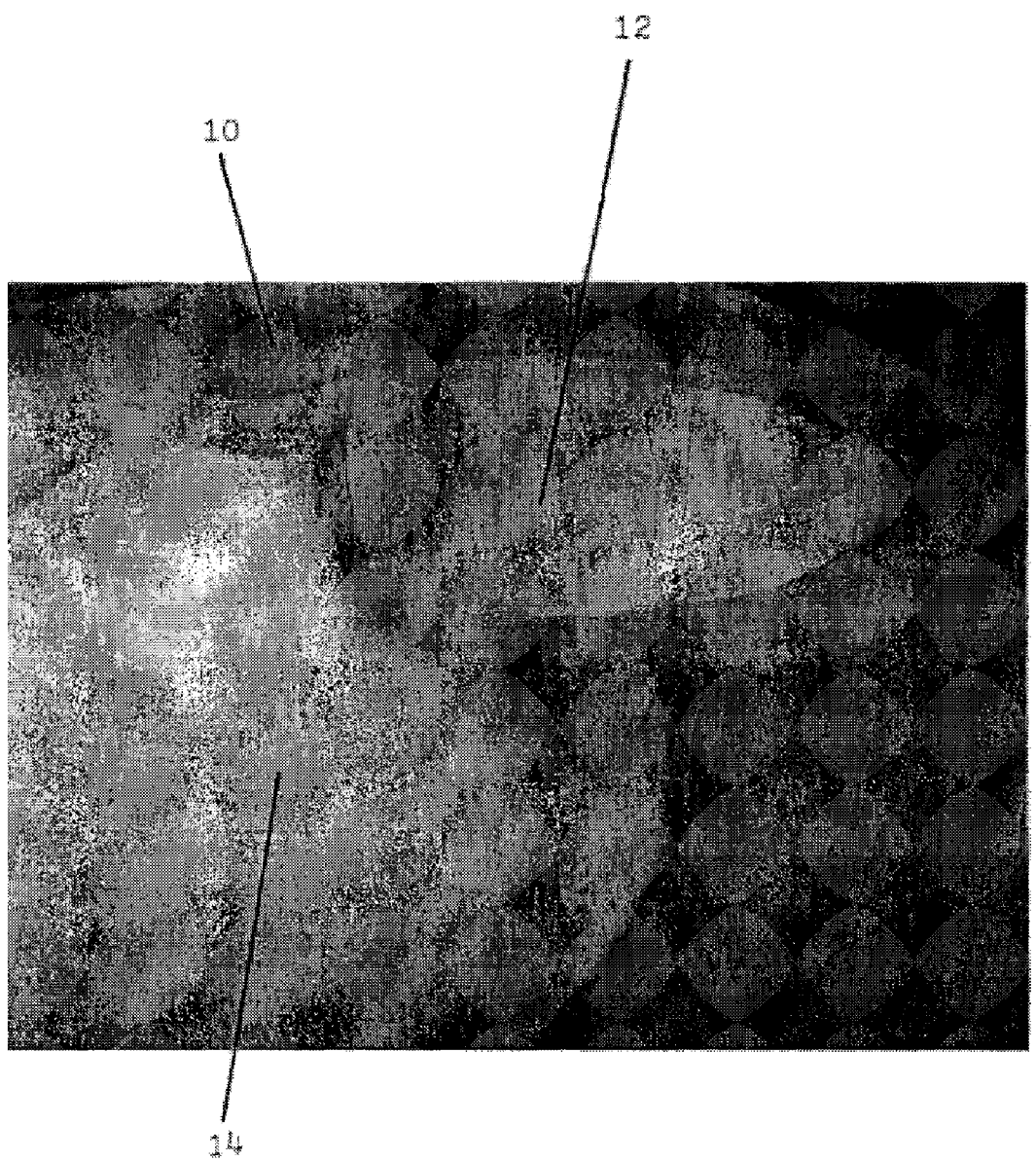
FIG. 7 is a view of the anatomically correct shape of the head cavity in the second embodiment of FIG. 6.
Figure 8:
FIG. 8 is a view of the anatomically correct shape of the torso recess in the second embodiment of FIG. 6.

A second example of the present invention is shown by FIGS. 6-8 respectively; and is a construction which is a complete rendering and recapitulation of the first embodiment described above, but is an article which has one additional structural feature. In this second format, the overall substance and appearance of the base substrate may be tapered or sloped over its length, width, and thickness dimensions; and this tapering effect results in a mattress pad which is slanted or inclined at a determinable angle from top surface to bottom surface and from front end to back end.

The inclined base substrate, as shown in the exemplary model of FIG. 6, is intended and expected to be a marked improvement over non-inclined versions; and will protect the supine positioned infant better against attacks of gastric reflux.

II. Configurational Details of the Molded Spatial Concanvities

The Head Cavity

The contours, volume and dimensions of the head cavity provide a molded and anatomically correct shape for receiving an infant's head. This aspect and detail of the invention is shown in detail by FIGS. 3 and 7 respectively.

As seen therein, the spatial outline of the head cavity shows its molded shape to be anatomically correct; and the separate discrete layers of material lining the interior of the spatial depression and forming the built-up outline for receiving the infant's head appear partially separated at the front of the cavity. Note that the neck bridge section (seen as a line of darker colored matter in FIG. 2) remains constant in height and physically separates the head cavity and torso recess portions of the orthotic device.

In this example, the width dimension of the base substrate is about 40 cm, and the length dimension is about 70 cm; and while the maximum thickness of the base substrate is about 75 cm, the thickness dimension at the deepest part of the head cavity {i.e. with all the individual layers of material removed from the cavity space} is about 10 cm.

The Anatomically Correct Shape of the Head Cavity

The anatomically correct head shape can be defined by mathematical derivation using standard head circumference charts [see for example, http://www.cdc.gov/growchai-ts]; and by assuming a normal cephalic index of 0.75.

Empirical measurements showed that a neck support of about 1.0 cm (as measured from upper back to midcervical spine) provided a comfortable position of neck extension to a newborn infant without causing excessive cervical lordosis {i.e., a curvature of the spine that is concave toward the rear). Also, to maintain the neutral neck lordosis, this relationship is increased to 2.0 cm by infant age 5 months. These measurements are derived from mean values, and will vary based upon individual head circumference. However, the ability to remove one or more discrete layers of material allows a parent or care-giver to adjust the overall spatial dimensions and volume of the cavity to accommodate and custom fit any infant's head.

An Exemplary Model

To illustrate this technical point even further, some examples of the altered and changed spatial volume and dimensional outlines for the head cavity, that are obtainable at will and can be created upon removal of one or more successive layers of material, are as follows:

The head cavity measures 8.8 cm wide, 9.0 cm tall, and 0.6 cm deep (from upper cervical spine to occipital prominence). These dimensions represent the anatomically correct size for a premature or small-for-age infant. All the removable at will layers of material are positioned in overlay series and are in proper place within the head cavity.

The head cavity measures 9.4 cm wide, 9.3 cm tall, and 0.9 cm deep (from upper cervical spine to occipital prominence). These dimensions represent the correct size for an average term infant. Layer 1 (the uppermost layer) has now been removed from the overlay series.

The head cavity measures 10.0 cm wide, 9.6 cm tall, and 1.2 cm deep (from upper cervical spine to occipital prominence). These dimensions represent the correct size for an average term infant of approximately 4 weeks of age. Layer 2 has also now been removed from the overlay series.

The head cavity measures 10.6 cm wide, 9.9 cm tall, and 1.5 cm. deep (from upper cervical spine to occipital prominence). These dimensions represent the correct size for an average term infant of approximately 8 weeks of age. Layer 3 has also now been removed from the overlay series.

The head cavity measures 11.2 cm wide, 10.2 cm tall, and 1.8 cm deep (from upper cervical spine to occipital prominence). These dimensions represent the correct size for an average term infant of approximately 12 weeks of age. Layer 4 has also now been removed from the overlay series.

The head cavity measure 11.8 cm wide, 10.5 cm tall, and 2.1 cm deep (from upper cervical spine to occipital prominence). These dimensions represent the correct size for an average term infant of approximately 4.5 months of age. Layer 5 has also now been removed from the overlay series.

Spaces or cut-outs intended for the ears of the infant are also lined with removable layers of material (confluent with the series of liners for the head) and are adjusted (widened in the cephlad/caudad dimension and deepened) as the occipital cavity deepens.

The Torso Recess

Figure 2:
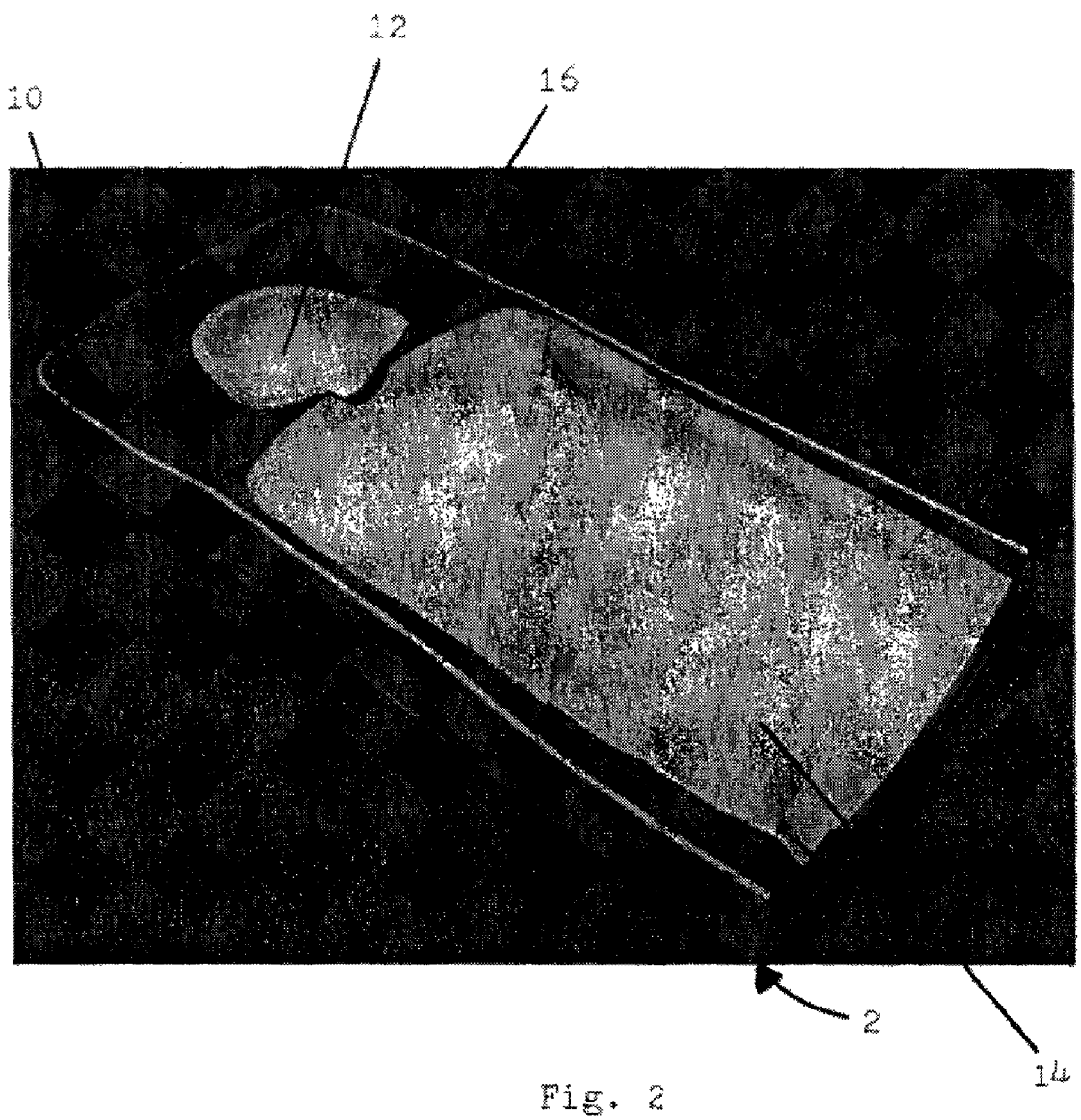
FIG. 2 is an overhead view of a first preferred embodiment of the orthotic device comprising the present invention.
Figure 3:
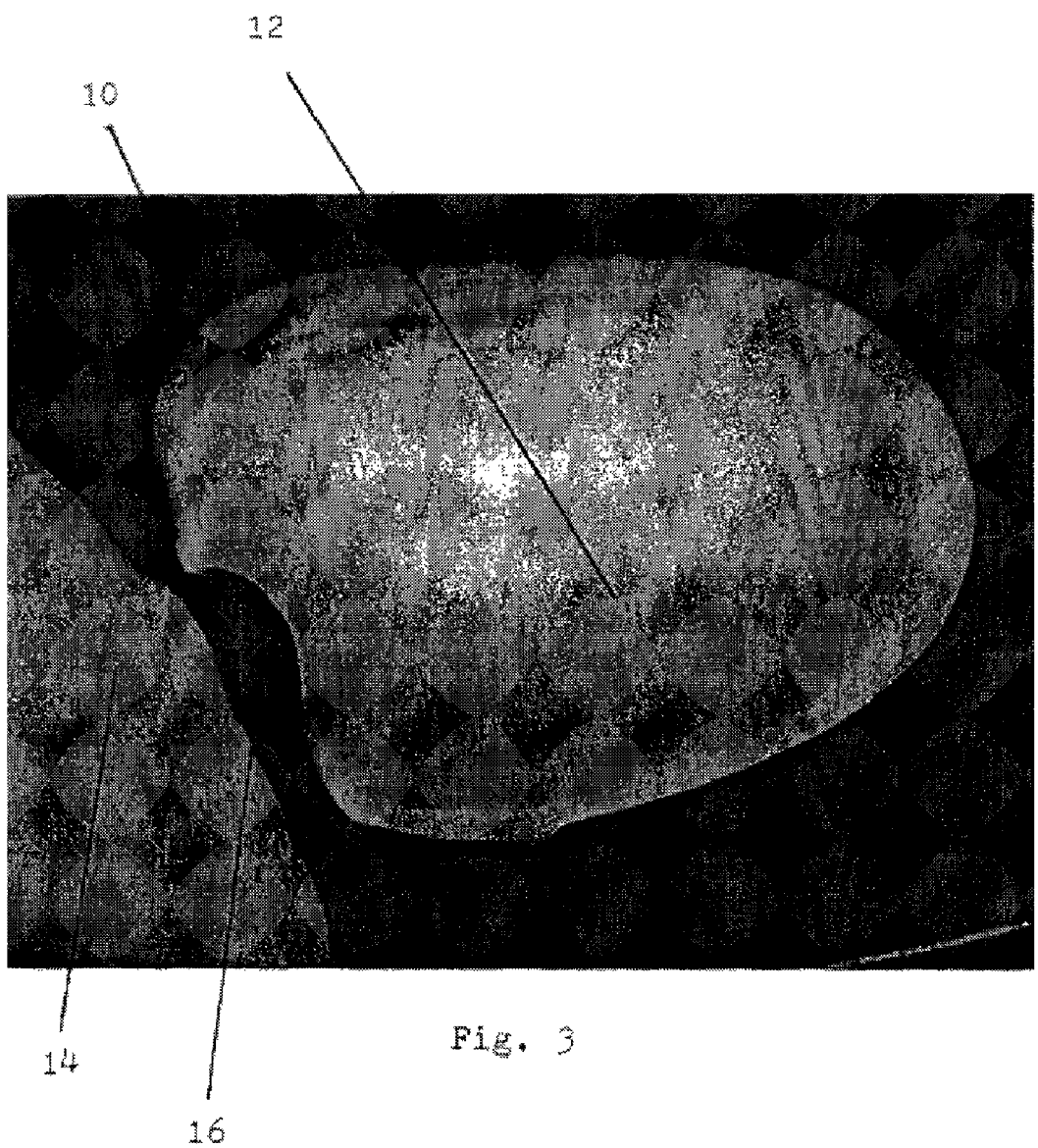
FIG. 3 is a view of the head cavity in the first embodiment of FIG. 2.
Figure 4:
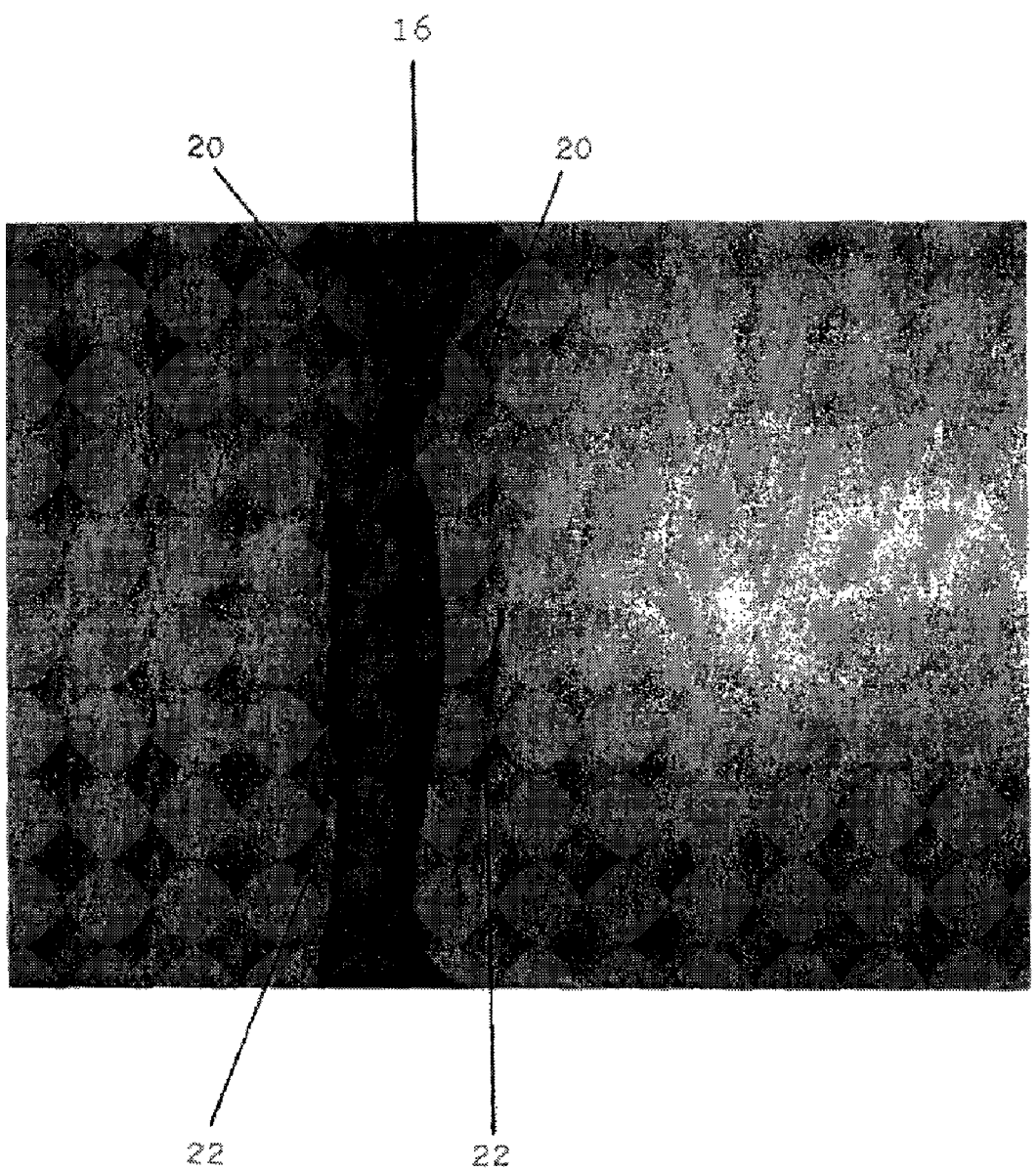
FIG. 4 is a view of the discrete layers of solid material lying within the head cavity and torso recess of the first embodiment of FIG. 2.
Figure 5:
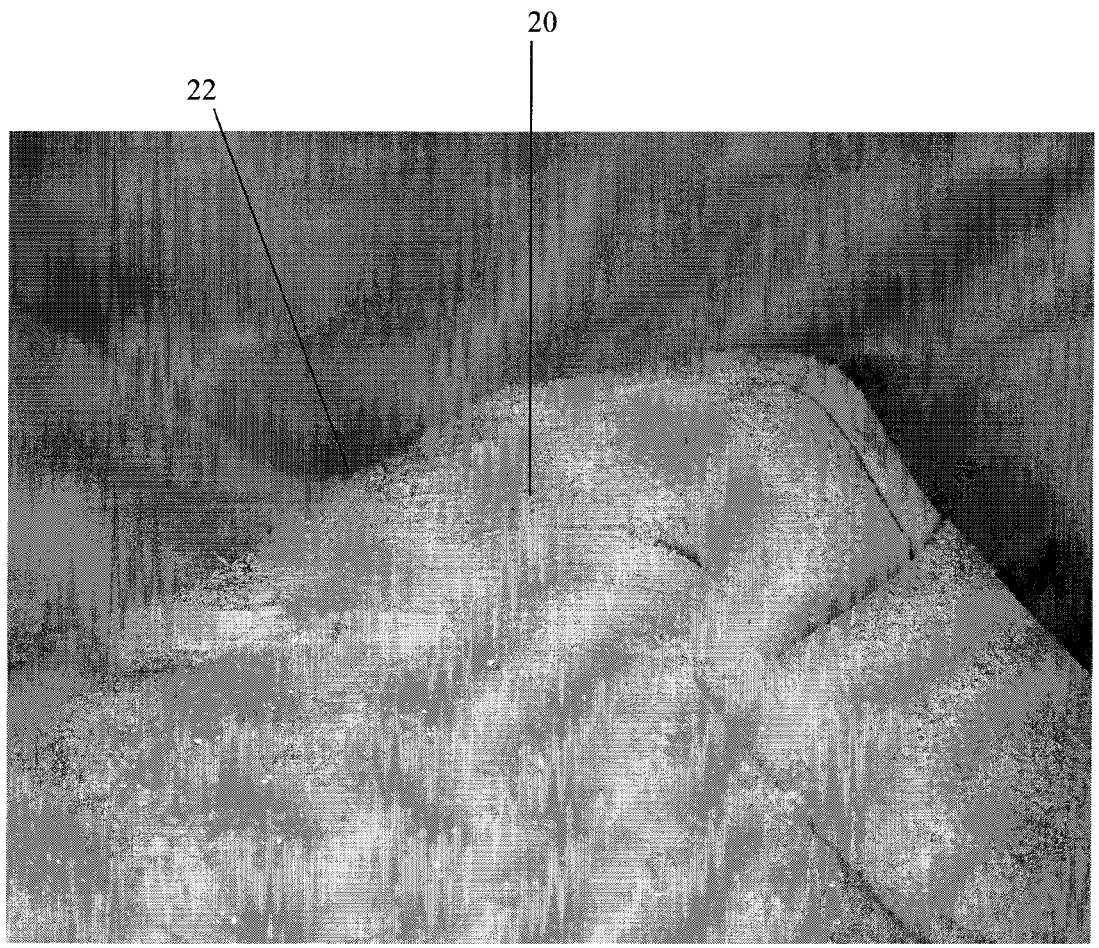
FIG. 5 is a detailed view of the discrete layers of solid material in the first embodiment of FIG. 2.

The overall shape and volume of the torso recess is sized to provide adequate width and length dimensions to receive and accommodate the infant's body. This is illustrated by FIGS. 2, 6, and 8 respectively.

The width and length dimensions of the preferred torso recess preferably will not and do not change as the depth dimension is adjusted and altered via the successive removal of individual layers of material. Thus, it is most desirable that the layers of material lining the spatial volume of the torso recess be arrayed in overlay series such that only the depth dimension of the concavity is affected when one or more individual layers of matter are removed.

An Exemplary Model

To illustrate this technical point even further, some examples of the altered and changed spatial volume and depth dimensions for the torso recess, that are obtainable at will and can be created upon removal of one or more successive layers of material, are as follows:

The torso recess measures 0.6 cm deep (from upper cervical spine to occipital prominence). These dimensions represent the anatomically correct size for a premature or small-for-age infant. All the removable at will layers of material are positioned in overlay series and are in proper place within the torso recess.

The torso recess measures 0.9 cm deep (from upper cervical spine to occipital prominence). These dimensions represent the correct size for an average term infant. Layer A (the uppermost layer) has now been removed from the overlay series.

The torso recess measures 1.2 cm deep (from upper cervical spine to occipital prominence). These dimensions represent the correct size for an average term infant of approximately 4 weeks of age. Layer C has also now been removed from the overlay series.

The torso recess measures 1.5 cm deep (from upper cervical spine to occipital prominence). These dimensions represent the correct size for an average term infant of approximately 8 weeks of age. Layer D has also now been removed from the overlay series.

The torso recess measures 1.8 cm deep (from upper cervical spine to occipital prominence). These dimensions represent the correct size for an average term infant of approximately 12 weeks of age. Layer E has also now been removed from the overlay series.

The torso recess measures 2.1 cm deep (from upper cervical spine to occipital prominence). These dimensions represent the correct size for an average term infant of approximately 4.5 months of age. Layer F has also now been removed from the overlay series.

Identification Aids for the Individual Layers of Material

It will be noted and appreciated also that, in order to facilitate the proper and correct usage of the orthotic device, the different and successive layers of material can be labeled, or coloreds or otherwise identified as to their proper placement, alignment, orientation within the arranged overlay series of discrete layers. Such labeling and identifications means may include:

π The age in weeks of an infant for which the individual layer is appropriate.

D The head circumference of an infant for which that layer is appropriate.

D Successive numbers (Arabic or Roman) or alphabet letters (English, Greek, or any other language) that correspond to instructions provided separately in written, audio, or video format.

D Differentiating colors that correspond to instructions provided separately in written, audio, or video format.

III. Alternative Embodiments of the Orthotic Device

A number of different designs and singular organizational formats can be employed as alternative embodiments of the orthotic device. All of these are deemed to be within the purview and scope of the subject matter as a whole which is the present invention.

A Head Rest Format

In this $1^{st}$ alternative format, the design of the head cavity and bridge section (supporting the neck) may be manufactured singly without any torso recess for use as a discrete head rest. An illustration of this alternative format and construction is shown by FIGS. 9 and 10 respectively.

Figure 9:
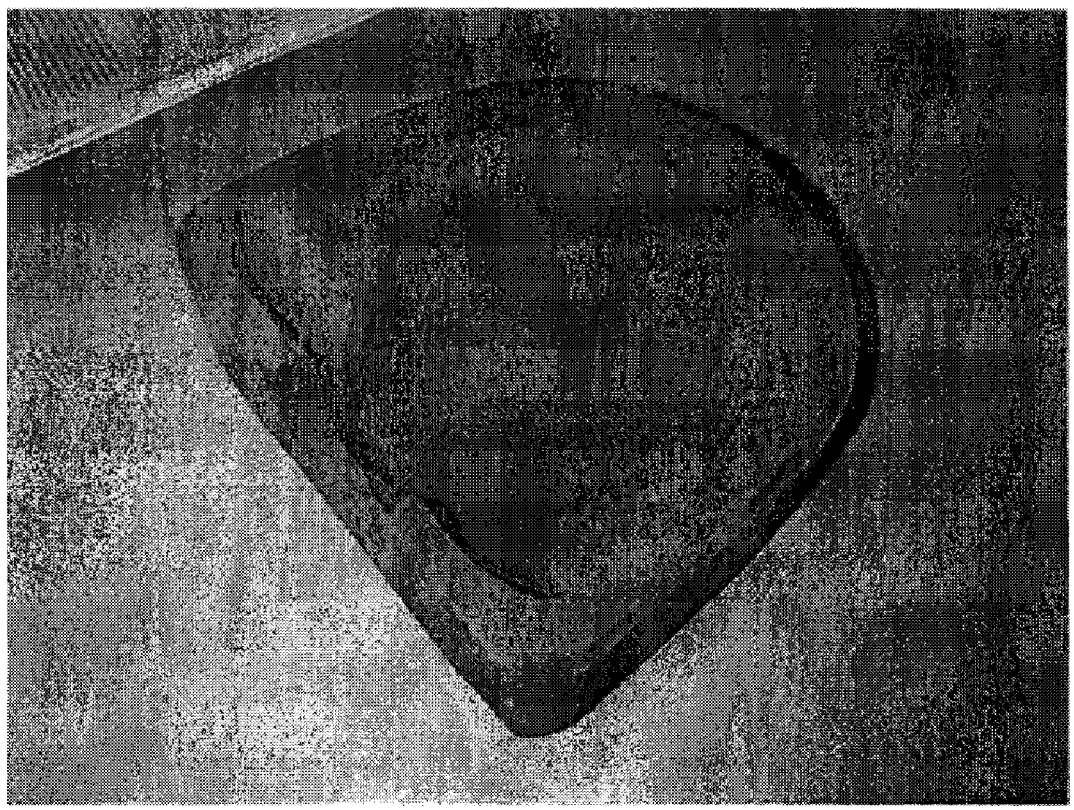
FIG. 9 is an overhead view of an alternative embodiment of the present invention wherein only a head cavity exists, without any torso recess being present.
Figure 10:
FIG. 10 is a frontal view of the alternative embodiment in FIG. 9.

As seen therein, this head rest format of the invention provides a head cavity only, with no torso recess as such, As shown by FIGS. 9 and 10, the multiple layers of material lining the spatial volume of the head cavity have been intentionally removed in order to visualize better the complete absence of any molded depression for the torso of the infant.

In this alternative structural construct, the head rest is format is the desired article. The head rest of FIGS. 9 and 10 may be placed on top of a mattress pad, a car seat, or any other resting surface. The infant's head is to be placed in the head cavity of the orthotic device, but the infant's torso and body must lie on the resting surface existing in-situ at that particular location. The infant's shoulders are supported by a small wedge that is tapered caudally. The distance between the neck bridge support and the infant's back does not change and cannot be adjusted. The bridge support for the neck protrudes about 10-1.5 cm from the upper back to off-load pressure between the infant's occiput and the resting surface in-situ.

Materials for the construction of this $1^{st}$ alternative embodiment, the head rest format, are as described generally below for preferred embodiments of the invention. Particular design specifications for the head cavity and the bridge support are as described earlier herein for the full mattress design.

A Re-Sculpted Spatial Depression Format

As a second alternative embodiment, an orthotic device comprising a base substrate having a head cavity and neck bridge support (with or without an accompanying torso recess) is custom made for the individual infant by a licensed orthotist. Because of the very precise adjustments permitted, this format of the orthotic device can be used to affect specific and individualized correction of occipital flattening. The construction is custom made and personally fitted to meet the infant's personal size specifications using the materials described hereinafter. Then, as the infant grows, the spatial volume, contours, and dimensions of the head cavity (and optionally the torso recess) is modified and enlarged repeatedly on multiple occasions, by the licensed orthotist to allow for calvarial expansion and infant growth over time.

Incorporation of the Invention into Infant Rest and Carriage Products

It is expected and intended that any or all of the different embodiments and formats of the present invention can be incorporated and be merged with a diverse range of other infant items; and that such collections can be prepared as an unified design and be produced as a single manufactured unit.

The typical variety of these other infant items is conventionally known and is commonly available from many commercial sources. These other infant items include, a bassinet; crib,; bed; carriage; pram; stroller; carrier; car seat; chair; high chair swing; rocker; mattress; mattress pad; diaper-hanging pad; or any other infant seating, resting, or carrying article.

IV. Suitable Materials for Constructing Any Format of the Orthotic Device

In preferred and alternative embodiments of the orthotic device, the entire manufactured mattress—including the base substrate, head cavity, torso recess, and neck bridge section—have been constructed and formed using individual, pre-sized layers of VOLARA® foam (a smooth surfaced, fine closed-cell structure, polyethylene foam). Specifically, the type of VOLARA® foam preferably used for manufacturing purposes is Grade EO closed-cell polyethylene foam having a density of 4 lbs. per cubic foot.

A number of other conventionally known and commercially available foams exist that are suitable for making the present invention. These alternatives include. Pelite; Plastizote; T-foam; or other formulated foams having physical and chemical properties similar to these.

As an additional guide, the essential properties that at least one foam material (of any known chemical composition or formulation) be employed, and that this foam should demonstrably provide and include, but are not be limited to, the following properties: (i) being a thermoformable material; and (ii) having a density substantial enough to maintain its integrity as a foam during physical load, but also being soft enough to allow long periods of use without causing adverse skin reactions.

In constructed prototypes of the molded head cavity and the torso recess in the mattress, 8 individual layers of foam have been used to advantage. In these instances, each individual foam layer is about 3-4 mm thick. However, it is expected and intended that each discrete foam layer may range from 2-6 mm in thickness; and that the total number of individual foam layers—arranged in overlay series to generate the configured head cavity and torso recess of the mattress—can vary from 3-12 discrete and separate foam layers.

VOLARA Foams

VOLARA is a federally registered trademark originally held by Voltek LLC (Lawrence, Mass.). However, Voltek LLC has been acquired by Sekisui America Corp.; and they now hold the trademark rights and commercially manufacture foam products at the same geographic location. Information concerning the grades and mechanical properties of the various VOLARA® foams that are commercially sold can be viewed at http://w.w.w.voltek.com/ma in.html.

VOLARA® foams are commercially sold in Grades A, EO, G, M, TS, AS, RS and VS. The basic differences among them are indicated by the data of Table 1 below. Also, the specifications for Grade EO VOLARA® foam are given by Table 2 below.

TABLE 1

VOLARA foams

| Grade | Properties |
| --- | --- |
| A | Mid Range; |
| EO | Flexibility & softness; |
| G | Increased flexibility & softness; |
| M | Higher temperature resistance, and stiffness; |
| TS | High strength tape substrate; |
| AS | Tough, enhanced vacuum formability; |
| RS | High performance pressure forming properties, high temperature resistance, and stiffness; |
| VS | High performance pressure forming properties, high temperature resistance, and stiffness. |

TABLE 2

Grade EO of VOLARA ® foam

| Specifications: | Closed cell/ethylene-ether foam/Type EO 4pcf |
| --- | --- |
| Color: | Black or white |
| Density: | 3.6-4.4 lbs/cubic foot |
| Compression strength (ASTM D3575): | 6 psi at 25%; 17 psi at 50% |
| Tensile strength, machine direction (ASTM D3575): | 140 psi |
| Tensile strength, cross-machine direction (ASTM D3575): | 99 psi |
| Elongation to break, machine direction (ASTM D3575): | 335% |
| Elongation cross-machine direction (ASTM D3575): | 362% |
| Tear resistance, machine direction (ASTM D3575): | 20 lbs./inch |
| Tear resistance, cross-machine direction (ASTM D3575): | 17 lbs./inch |
| Compression set (ASTM D3575): | 11% of original thickness |
| Shore hardness (ASTM D2240), A scale: | 10 |
| Shore hardness (ASTM D2240), OO scale: | 51 |
| Thermal stability, 24 hrs. at 158° F., machine direction: | −1.7% maximal |
| Thermal stability, 24 hrs. at 158° F., cross-machine direction: | −1.2% maximal |
| Thermal conductivity K factor at 70° F.: | 0.30 BTU/(hr)(ft2)(° F./in) R Factor − Thickness/ K Factor |
| Water absorption, (ASTM D1667): | 0.04 lbs/sq. foot |

The base substrate of the manufactured mattress (the planar tier holding and maintaining the head cavity and the torso recess as discrete spatial depressions, and forming the substance of the supporting material) is preferably constructed of VOLARA® foam type 12AW, having a density of 12 lbs. per cubic foot. Other alternative closed cell foams that may be used in making the base substrate of the molded mattress are Pelite, Plastizote, T-foam, or other foams having a density of approximately 12 lbs per cubic foot.

Equally important, the chosen foam employed as the material for the base substrate must be thermoformable. In preferred embodiments of the pre-molded mattress, the maximal girth of the base substrate in the mattress is typically about 75 mm in thickness—because the base substrate material of the mattress must be sufficiently thick to support the infant's head and torso when placed into the molded spatial cavities prepared for them. Accordingly, for this purpose, it is also expected that the foam used for the base substrate may vary in overall thickness from about 50-100 mm.

V. The Intended Method for Using the Orthotic Device

The prepared pad or mattress comprising the present orthotic device is designed for infants ranging in age from birth up to 4 months of age. This time frame is medically considered to be the most critical. It is therefore recommended that the infant be placed in the orthotic device—regardless of whether it be in the form of a pad, mattress or pillow—on each occasion that the infant is placed at or lies in a supine position, or when the infant's occiput could make contact with a flat surface (e.g., a car seat, stroller, etc.).

The orthotic device is intended for and is expected to be used with infants below 4 months of age, since such infants usually lack sufficient motor control to roll over or otherwise escape from the pad, mattress or pillow. Infant mobility after about 4 months of age usually precludes successful use of the medical device. If there is significant head asymmetry or flattening in an infant older than 4 months, a molding helmet should be considered.

Specific instructions and advice for the use of the orthotic device of the present invention can be provided to parents and child caretakers. Such instructions and advice can be provided in written, audio, or video form; and will typically include the following:

How to adjust the bed, pad or mattress article in order to provide the best possible fit for each infant individually.

A listing of specific times (hours per day) considered to be best and highly recommended for use.

Guidelines for when to remove one or more discrete layers of solid material from each array of layers then disposed within the head cavity and torso recess.

Tools and aids for measuring the infant's head and torso in order to facilitate the timing of the removal of single layers of material from the head cavity and torso recess.

Instruments with which to measure to the extent of posterior plagiocephaly initially and by which to determine the degree of rounding improvement in the head shape of the infant over time.

IV. Clinical Experience and Resulting Empirical Data

To demonstrate the merits and value of the present invention, a series of planned experiments and empirical data are presented below. It will be expressly understood however, that the experiments described herein and the results provided below are merely the best evidence of the subject matter as a whole which is the present invention; and that the empirical data, while limited in content, is only illustrative of the scope of the present invention as envisioned and claimed.

An illustrative recitation and representative example of the present invention is the preferred manner and mode for practicing the methodology is also presented below as part of the experimental method. It will be expressly understood, however, that the recited steps and manipulations presented below are subject to major variances and marked changes in the procedural details; all of which are deemed to be routine and conventional in this field and may be altered at will to accommodate the needs or conveniences of the practitioner.

The Clinical Study

The initial prototype of the orthotic device—described as alternative embodiment 2 previously herein—was used to treat plagiocephaly clinically in infants younger than 4 months of age (at the time of initial evaluation). All patients participating in the study were evaluated and treated in the practice of Dr. Gary F. Rodgers, Division of Plastic Surgery, Children's Hospital Boston (Boston, Mass.).

Materials and Methods

Twenty Six (26) patients underwent treatment of plagiocephaly using a customized and individually fitted head cavity [there was no torso recess as such in the orthotic device]. Each head cavity was prepared and individually adjusted in spatial volume and size dimensions by licensed orthotists from the National Orthotic and Prosthetic Company (Boston Brace).

A control group of 23 infants diagnosed with plagiocephaly, prior to the present study, were treated and managed only using parental positioning of the infant; and these data were available for use as a comparison basis. The gestation age, age at initial examination, and age at follow-up examination, were all recorded. All patients underwent pre- and post-treatment cephalometric evaluation of the transcranial difference (a measure of the calvarial obliquity) using head calipers. Statistical analysis of all variables was performed using SAS software.

Empirical Results

The mean transcranial different in the treatment group using the present orthotic device improved from 11.3 mm to 3.4 mm over an average treatment time interval of 70.4 days. In comparison, the mean transcranial difference in the earlier control group showed an improvement from 9.0 mm to 8.0 mm, over a mean treatment time interval of 61.6 days. The difference was statistically significant (p=0.000).

The variables that were found not to be statistically significant included.

gestation age (39 weeks control group, 38 weeks treatment group; p=0.052);

age at initial evaluation (88 days control group, 98 days treatment group; p=0.177);

initial transcranial differences (9 mm control group, 11.3 mm treatment group; p=0.057);

differences in neck rotation at initial evaluation (38 degrees control group, 43.7 degrees treatment group; p=0.276);

neck rotation at final examination (13.9 degrees control group, 15.4 degrees treatment group; p=0.451);

days from initial examination to final examination (61.6 days control group, 70.4 days treatment group; p=0.69).

CONCLUSIONS

The present orthotic device comprising a head cavity which is adjustable in its dimensions and available spatial volume is highly effective in clinically restoring normal head symmetry for infants under 4 months of age. In comparison, the technique of positioning and re-positioning the infant as he ties in a supine position was clinically ineffective.

The present invention is not to be limited in form nor restricted in scope except by the claims appended hereto.

What we claim is:

1. A method for treating posterior plagiocephaly in an infant comprising an orthotic bed comprising:

a base substrate having fixed dimensions and configuration;

an anatomically correcting concave head cavity molded into said base substrate able to receive and support the occiput of an infant's head;

a plurality of discrete layers of foam material serving as a series of prepared individual layers positioned one over the other as multiple strata in overlay array series within the molded spatial volume of said concave head cavity, said layers being individually removable at will from the positioned overlay series lying within the spatial volume of said head cavity, and, via their presence within said concave head cavity, can alter the available spatial volume presented by said head cavity for the occiput of an infant's head; and a bridge section adjacent to said head cavity serving to support the neck of a infant and to off-load pressure between the infant's occiput and the resting surface of the head cavity;

a concave torso recess molded into said base substrate able to receive and support the torso of an infant's body; and a plurality of discrete layers of foam material serving as a series of prepared individual layers positioned one over the other as multiple strata in overlay array series within the molded depth dimension of said concave torso recess, said layers being individually removable at will from the positioned overlay series lying within the molded depth dimension of said concave torso recess, and, via their presence within said torso recess, can alter the available dimensional depth presented by said torso recess for supporting an infant's torso;

said method, comprising placing an infant into said bed, wherein said infant is up to 4 months in age and has occipital flattening, such that said infant's head contacts said concave head cavity and pressure between the infant's occiput and the resting surface of the head cavity is off- loaded by said bridge, resulting in progressive normalizing and rounding of said infant's occipital region.

2. The method of claim 1, wherein said infant is placed in said bed to prevent permanent plagiocephaly.

3. The method of claim 1, wherein said infant has plagiocephaly and is placed in said bed to correct the shape of the infant's occiput.

4. The method of claim 1, wherein during said progressive normalizing and rounding of said infant's occipital region, one or more of the plurality of discrete layers within said concave head cavity are removed to accommodate growth of said infant.

\* \* \* \* \*